United States Patent [19]

Sarstedt

[11] Patent Number: 5,095,914
[45] Date of Patent: Mar. 17, 1992

[54] BLOOD EXTRACTION DEVICE WITH ONE-WAY PISTON MOVEMENT

[75] Inventor: Walter Sarstedt, Nuembrecht-Rommelsdorf, Fed. Rep. of Germany

[73] Assignee: Walter Sarstedt Geraete und Verbrauchsmaterial fuer Medizin & Wissenschaft, Nuembrecht-Rommelsdorf, Fed. Rep. of Germany

[21] Appl. No.: 587,697

[22] Filed: Sep. 25, 1990

[30] Foreign Application Priority Data

Sep. 26, 1989 [DE] Fed. Rep. of Germany ....... 3932109

[51] Int. Cl.$^5$ .............................................. A61B 5/00
[52] U.S. Cl. ...................................... 128/765; 604/220
[58] Field of Search ...................... 604/110, 220, 209; 128/760, 763, 765

[56] References Cited

U.S. PATENT DOCUMENTS

| | | | |
|---|---|---|---|
| 201,443 | 3/1878 | Parker | 604/209 |
| 2,369,304 | 2/1945 | Lewis | 604/209 |
| 4,246,898 | 1/1981 | Travalent et al. | 604/220 X |
| 4,333,457 | 6/1982 | Marqulies | 604/110 X |
| 4,370,987 | 2/1983 | Bazell et al. | 128/760 |
| 4,459,997 | 7/1984 | Sarstedt | 604/110 X |
| 4,642,102 | 2/1987 | Ohmori | 604/210 |
| 4,832,696 | 5/1989 | Luther et al. | 604/164 |
| 4,840,616 | 6/1989 | Banks | 604/110 |
| 4,906,231 | 3/1990 | Young | 604/110 |
| 4,978,339 | 12/1990 | Labouze et al. | 604/110 |

FOREIGN PATENT DOCUMENTS

| | | | |
|---|---|---|---|
| 0012528 | 7/1903 | Fed. Rep. of Germany | 604/209 |
| 0669910 | 4/1989 | Switzerland | 604/110 |
| 8900432 | 1/1989 | World Int. Prop. O. | 604/110 |

Primary Examiner—Max Hindenburg
Attorney, Agent, or Firm—Townsend and Townsend

[57] ABSTRACT

A blood extraction device features an extraction cylinder (11) having a forward end for attaching a needle (12) and a rear end having an opening (13) for a piston rod (14) together with a piston (15) secured to the forward end of the piston rod (14) arranged to slide axially in the extraction cylinder (11). The piston (15) can essentially be moved only in the direction away from the forward end of the extraction cylinder (11) and practically incapable of being moved when subjected to a force in the direction of the forward end due to one-way coacting means of prevention (17, 18).

16 Claims, 4 Drawing Sheets

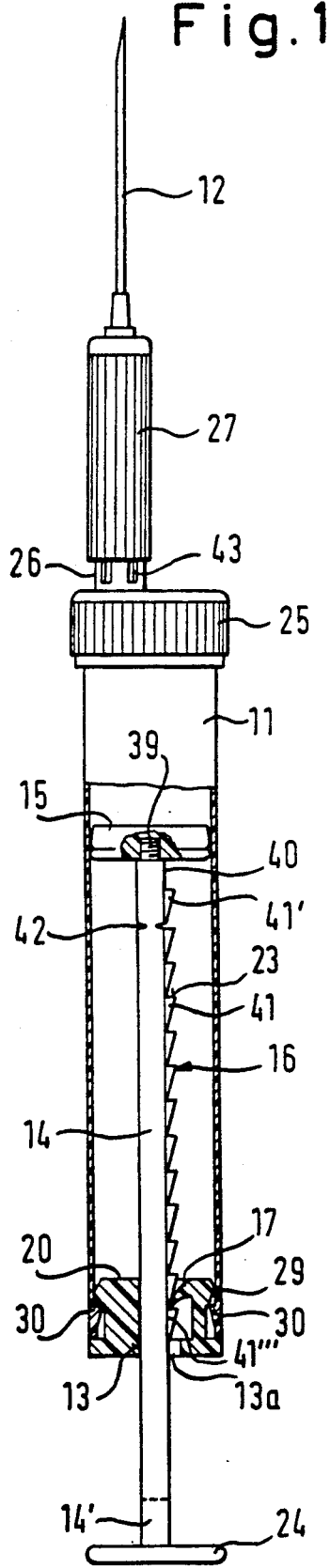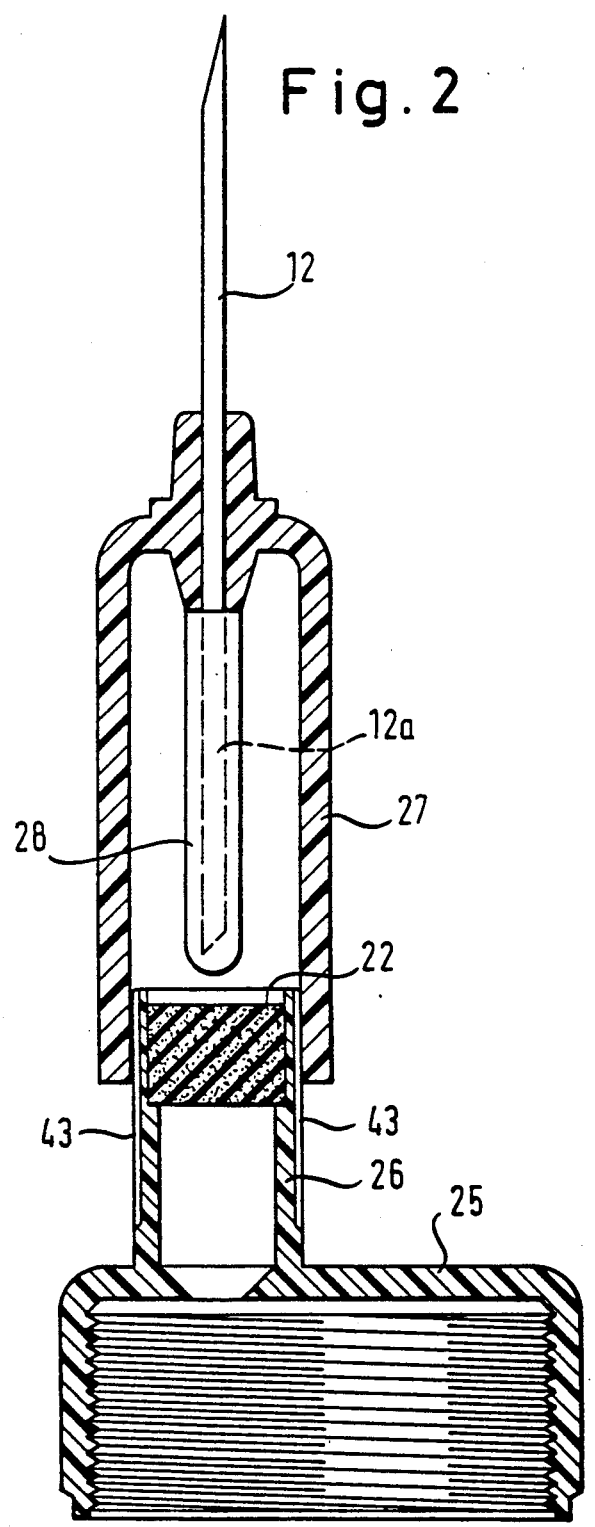

BLOOD EXTRACTION DEVICE WITH ONE-WAY PISTON MOVEMENT

BACKGROUND OF THE INVENTION

1. Field of the Invention

The invention relates to a blood extraction device and more particularly to a blood extraction device having a piston that can be moved in either direction for testing purposes and substantially only in the direction away from the needle when used to extract blood.

2. Description of the Prior Art

Blood extraction devices (see e.g. DE-PS 29 48 653, 30 49 503) are intended merely to extract blood from, but not to inject any kind of fluid substance into the vein of the patient, although they are generally suitable for this purpose.

In conjunction with disposable syringes it is prior art (DE-Gbm 88 04 656) to prevent repeated use by ratchet means allowing only one charging of the syringe and one injection but not a repeat charging with fluid. For this purpose, however, the barrel of the syringe must be provided with a ratchet ring in the form of a piston sliding with friction within the syringe barrel.

In a further disposable syringe of prior art (U.S. Pat. No. 4,826,483) the piston rod is provided with a plurality of ratchet keys which interact with spring-loaded ratchet shoulders at the bottom of the syringe. By turning the piston rod thru 90° the syringe can be charged and then the fluid injected into, for example, the vein of the patient. Since further turning of the piston rod is prevented by the ratchet key locking into place in a radial notch of the piston rod, this syringe too can only be used once for charging with liquid and injecting this liquid.

Also known as prior art is a blood extraction device (U.S. Pat. No. 4,370,987) the piston rod of which is toothed and the rear end of which has an opening for passage of the piston rod and a stop arranged therein. This is intended to establish the position of the piston in various charging positions to enable a vacuum of prescribed strength to be created in the cylinder. As soon as the vacuum is created in the cylinder the rear sharpened end of a needle inserted in the vein of the patient can be used to puncture a flexible plug located in the forward end of the cylinder thus allowing the vacuum to become active within the needle and draw the blood from the vein of the patient.

However, in this blood extraction device of prior art the opening for passage of the piston rod in the rear end of the cylinder must be so large that the toothing on the piston rod and the stop could possibly disengage thus making it possible to push the piston also forwards which is also intended to eject the received blood into some other receiving vessel. This device of prior art could thus also be misused as a syringe.

SUMMARY OF THE INVENTION

This invention is thus based on the device according to U.S. Pat. No. 4,826,483 which is also suitable for blood extraction in which the piston rod is guided in the axial direction relative to the extraction cylinder so that the one-way coacting means cannot be disengaged by radial movements of the piston rod, but only by turning of the piston rod.

On the basis of a device of this kind the object of the invention to create a blood extraction device of the aforementioned kind, the use of which as a syringe is rendered impossible, to safely preclude any intentional misuse of the blood extraction device as a syringe.

The achievement of this object can be seen from the features of the embodiments of the present invention described below.

Moving the piston in the direction of the forward end of the extraction cylinder is possible in the utmost situation at best to the extent that a certain, but exceptionally slight travel of the piston in this direction is necessary to cause the one-way coacting means comprising, for example, a ratchet toothing and an interacting ratchet key to be effective. The movement of the piston in the forwards direction necessary to engage the one-way coacting means must be as slight as possible, however, and in particular so slight that this would cause only part of the blood present in the needle, at the utmost, to be forced back into the vein, but no part of the content of the extraction cylinder.

One advantageous embodiment is formed so that the one-way coacting means are arranged between the piston rod and the rear end of the extraction cylinder.

In this arrangement the one-way coacting means can comprise at least one ratchet toothing running along and located on the piston rod and at least one ratchet stop to interact with the toothing at the rear end of the extraction cylinder, whereby the ratchet toothing should be so fine that no substantial movement of the piston forwards is necessary to cause the stop to engage in the toothing.

In a first alternative of this embodiment the arrangement can be such that the teeth of the ratchet toothing are non-elastic and the ratchet stop has spring-loaded contact on the ratchet toothing by being configured as a ratchet key.

It is, however, particularly advantageous to provide the teeth of the ratchet toothing as spring lugs slanting forward away from the piston rod to interact with a fixed ratchet shoulder constituting the ratchet stop and extending at right angles to the elongation of the piston rod it being good practice to commence the ratchet shoulder at such a radial distance away from the piston rod that the spring lugs in spring contact with the piston rod are able to pass through the gap between the piston rod and the ratchet shoulder. Particularly effective one-way coacting means are achieved when the ratchet shoulder translates in a radial spacing away from its commencement to a wall extending rearwards which prevents the radial expansion, and thus negating the ratchet action, of the spring lugs snapping directly into place behind the ratchet shoulder when the piston rod is moved forwards. This embodiment is particularly favourable when the end of the extraction cylinder is in one piece since in this case providing a spring-loaded ratchet key at this location can be something of a problem. On the other hand, the spring lugs can be produced on the piston rod with no problem during manufacture.

A further embodiment which makes the arrangement of ratchet toothing on the piston rod dispensible is characterized by the one-way coacting means comprising a one-way locking means located at the end of the extraction cylinder acting together with the opposing, preferably roughened surface of the piston rod. These locking means permit continuous locking of the piston or the piston rod in the sense that practically no movement of the piston or the piston rod forwards is necessary for the one-way coacting means to be effective. To create a particularly favourable constructional embodiment of the rotational control means provided originally and non-removably the invention provides according to a first alternative the rotational control means to be formed by ratchet toothing mating in a radial notch having side flanks and arranged unfree to turn with respect to the extraction cylinder or by the piston rod having an unround cross-section passing through a suitable unround guide opening at the rear end of the extraction cylinder.

Instead of rotational control means it can be provided for in the sense of a second embodiment of the present invention that the piston rod is roughened on all sides and the locking means are arranged around the piston rod.

For the purpose of rational assembly of the blood extraction device according to the invention in production one preferred embodiment of the invention provides for the one-way coacting means at the rear end of the extraction cylinder having a plug for insertion in or on the rear end of the extraction cylinder and featuring a guide opening for the piston rod and which can be fixed in the end of the extraction cylinder so that it remains in position when removing or inserting the piston rod from and into the extraction cylinder respectively.

In this arrangement the plug is provided for locked insertion in the rear end of the extraction cylinder so that it cannot be removed without being destroyed even when being manipulated by means of a tool, thus effectively preventing any misuse of the blood extraction device according to the invention as a syringe.

It is basically sufficient to provide the plug on one side of the piston rod, however, it is preferable to provide the plug so that it extends completely around the piston rod.

To enable a ring-type locking plug of this kind to be assembled easily during manufacture it can be provided either axially split into two halves thus permitting insertion to enclose the piston rod or it is configured so that is can be pushed into place on the piston rod from the piston end when one-way coactive means are used which are rendered useless by a tool, in which case however the piston can be removed from time to time for instance by unscrewing.

Another possibility of assembly is provided by arranging for the handle or rear end-piece of the piston rod to be removable or, in particular, unscrewed so that the plug can be inserted on the piston rod at its rear end.

Of particular advantage is to provide the invention as a blood extraction device with the forward end of the extraction cylinder closed off by a pierceable diaphragm, the latter being preferably provided in a boss of a screw cap screwed on to the forward end of the extraction cylinder (DE-C2-29 48 653). This boss is used to mount a guide sleeve holding a needle sharpened at both ends, the rear end of the needle piercing the diaphragm.

In general one preferable method of vacuum-testing the device is characterized by the rearwards movement of the piston necessary for vacuum-testing being achieved with the plug still to be inserted in the rear end of the extraction cylinder but preferably already arranged on the rear end of the piston rod and the plug not attaining its final position at the rear end of the extraction cylinder until the piston has been pushed into its forward end position after or during vacuum-testing.

Vacuum-testing is preferably carried out so that the piston is first pushed sufficiently forward into the vented forward end of the extraction cylinder so that the plug is just about to attain its final, in particular, locked position at the rear end of the extraction cylinder, the forward end of the latter then being sealed, the piston then being returned somewhat and preferably rereleased to enable its return into more or less its original position to be monitored when the vacuum has been produced, the plug on completion of successful vacuum-testing being located, in particularly, locked in place at the rear end of the extraction cylinder.

When a blood extraction device of this kind has been produced in manufacture, vacuum-testing can also be done by briefly retracting the piston. After vacuum-testing movement of the piston forwards results in evacuation of the space of the extraction cylinder ahead of the piston, e.g. by briefly unscrewing a forward screwed cap.

This procedure can be combined when inserting the plug in the blood extraction device according to the invention, by the plug still not being inserted in the rear end of the extraction cylinder during vacuum-testing by retracting the piston but preferably already being arranged over the rear end of the piston rod and by the plug being forced into the fitted position when subsequently venting, a projection on the piston rod or the rearmost tooth of the ratchet toothing or the handle at the end of the piston rod transmits the pushing force to the plug, in particular. Thus pushing the plug into the rear end of the extraction cylinder is done in the same procedure as for evacuating (venting) the internal space of this cylinder.

BRIEF DESCRIPTION OF THE DRAWINGS

The invention will be now described in the following for example with reference to the drawing in which:

FIG. 1 is a partly sectioned side view of a blood extraction device in accordance with the invention FIG. 2 is a partly sectioned, enlargened side view of the screw cap located on the forward end of the extraction cylinder according to FIG. 1 showing the components provided

DETAILED DESCRIPTION OF THE PREFERRED EMBODIMENT

Figure 3:
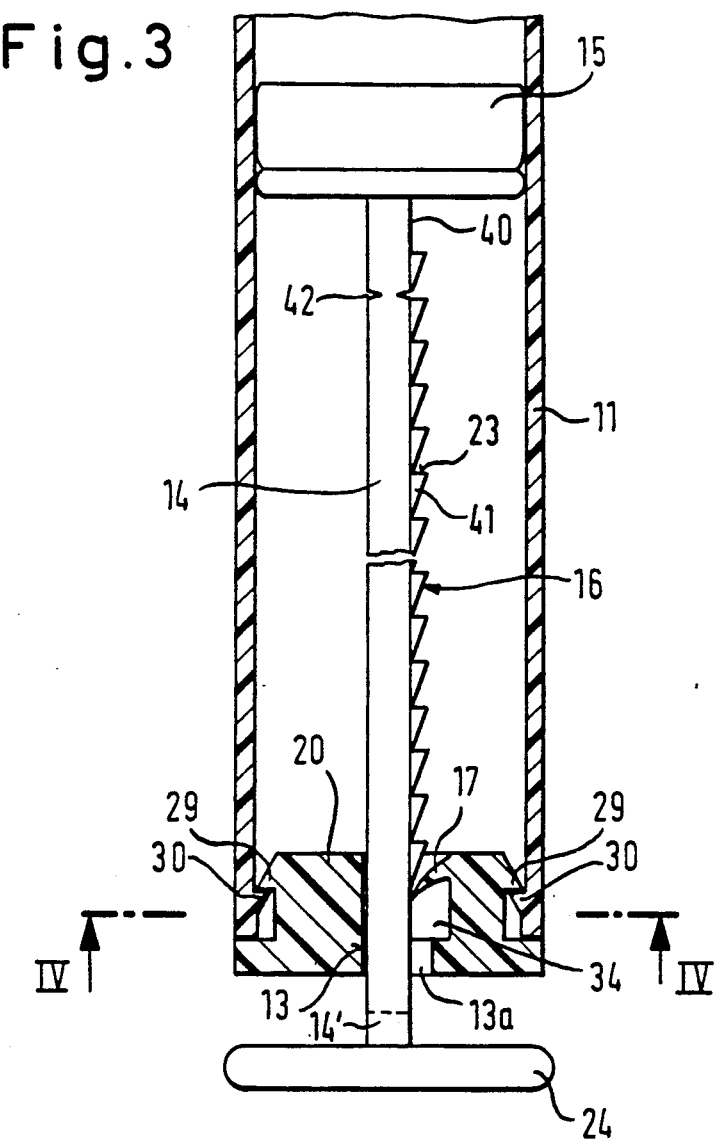
FIG. 3 is a slightly enlargened, partly sectioned side view of the region of the blood extraction device incorporating the one-way coacting means (with reference to FIG. 1)

FIG. 1 shows a rotationally cylindrical extraction cylinder 11 with a screw cap 25 for screwing on to the male thread at its forward end from which a boss 26 extends forwards as shown in FIGS. 1 and 2 in which a piercable diaphragm 22 is arranged. On the rotationally cylindrical hollow boss 26 a guide sleeve 27 having a rotationally cylindrical interior can be mounted, said sleeve holding at its forward end a needle 12 sharpened at both ends, the rear part 12a of which is covered by a flexible tubing 28. In the outer surrounding surface of the boss 26 axial vent grooves 43 are provided.

When mounting the guide sleeve 27 as shown from the position in FIG. 2 the rear end of the needle part 12a pierces the tubing 28 and then the diaphragm 22 thus producing a connection from the forward end of the needle 12 to the interior of the boss 26 and thus to that of the extraction cylinder 11. As soon as the guide sleeve 27 is removed from the boss 26 and part 12a of the needle 12 removed from the diaphragm 22 the tubing 28 automatically envelopes the rear part 12a of the needle 12, whilst the penetration in the diaphragm 22 automatically closes due to the elasticity of the diaphragm.

In the extraction cylinder 11 a piston 15 is arranged as shown in FIGS. 1 and 3 to slide axially tight, into which a piston rod 14 is screwed from the rear at 39 and carrying on the one side as shown in FIGS. 1 and 3 a ratchet toothing 16 extending parallel to the center-line of the piston rod 14, the teeth of which (41) feature a ratchet surface 23 at their end extending essentially vertical to the piston rod 14 whilst slanting to the rear of the piston rod 14.

As shown by FIGS. 1 and 3 an annular plug 20 is inserted in the rear end of the extraction cylinder 11, this plug featuring an axial guide opening 13 for the piston rod 14 and also provided with a spring-loaded ratchet key 17 opposing the ratchet toothing 16. The teeth of the ratchet toothing 16 and of the ratchet key 17 are inclined so that when the piston rod 14 is retracted from the extraction cylinder 11 the ratchet key 17 can detent in one tooth to the next, whilst any attempt to move the piston rod 14 in the direction of the screw cap 25 forces the ratchet key 17 against the ratchet surface 23 of the tooth 41 in place at that time of the ratching toothing 16 thus blocking movement of the piston rod 14 in this direction. The piston rod 14 is held in the guide opening 13 so that it cannot escape from the ratchet key 17. For this purpose the guide opening 13 is formed as shown in FIGS. 1 and 3 so that smooth side of the piston rod 14 facing away from the ratchet toothing 16 is in contact with the wall of the guide opening 13. Diametrically opposed is the passage at 13a somewhat larger to create sufficient room to allow the ratchet toothing 16 to pass and connecting the ratchet key 17 axially to the rear.

It is particularly important that the ratchet key 17 is released, i.e. not located at the level of the ratchet toothing in the basic position as shown in FIG. 3. In this way the ratchet key 17 will not lose its spring force even when the blood extraction device is shelved for a lengthy period.

The plug 20 features locking projections 29 extending radially outward so as to mate with the rear of the companion ratchet projections 30 on the rear end of the extraction cylinder. The ratchet projections 29 and those of the companion ratchet 30 have precisely the reverse ratchet effect to that of the ratchet toothing 16 and the ratchet key 17, i.e. to allow the plug 20 to be inserted from the rear into the extraction cylinder 11 in the direction of the screw cap 25 where it locks into place, whilst axial retraction of the plug 20 to the rear is prevented by the ratchet projections 29 acting together with the companion ratchet 30.

At certain positions around the companion ratchet 30 radial notches 31 (FIG. 4) can be provided to mate the radial projections 32 of the plug 20 to prevent the plug 20 from turning in the extraction cylinder 11.

Figure 4:
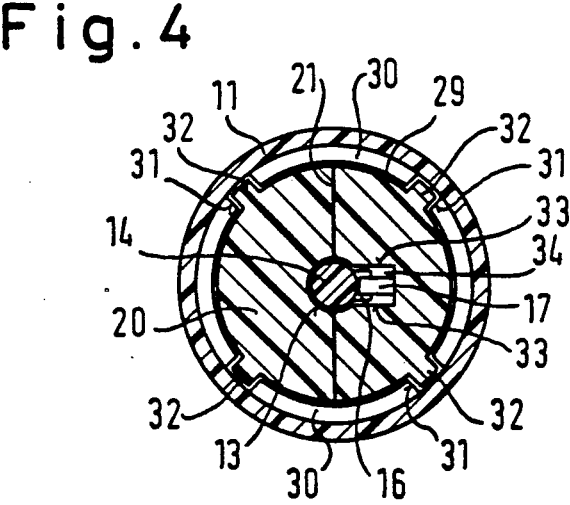
FIG. 4 is a section along line IV—IV in FIG. 3

Rotation control means of this kind are necessary—as shown in FIGS. 1, 3 and 4—to the extent that the ratchet toothing 16 and the ratchet key 17 are provided on one side of the piston rod 14 only. Any other means of rotational control can be used for the plug 20 to ensure that the ratchet toothing 16 and the ratchet key always remain true.

So that the piston rod 14 assumes the correct rotary position with respect to the plug 20, the side flanks 33 (FIG. 4) of a radial recess 34 in the plug 20 in which the ratchet key 17 is accommodated can act together with the ratchet toothing 16 to produce a suitable rotational control. In accordance with the invention, therefore, the plug 20 is located in relation to the extraction cylinder 11 and the piston rod 14 relative to the plug 20 in the prescribed rotational position.

Figure 5:
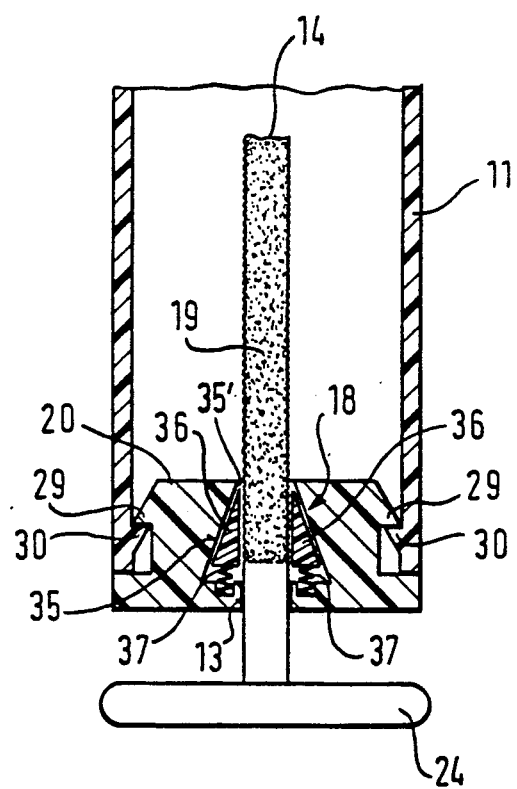
FIG. 5 is a partly sectioned side view analogous to FIG. 3 showing the one-way coacting means in the form of locking means and FIG. 6 is a view similar to FIG. 3 showing a similar arrangement of the one-way coacting means.

In the embodiment as shown in FIG. 5 diametrally opposed surfaces of the piston rod 14 are provided with a roughened surface 19. In the inside of the port 20 locking means constituting complemantary wedges 36 in forward tapering wedge-shaped recesses 35' are provided. These wedges 36 are in friction contact by their radial inside surfaces with the surface 19 of the piston rod 14 by being forced forward due to the springs 37. When the piston rod 14 is removed from the screw cap 25 the wedges 36 lose contact with the wedging 35 tapered in the direction of the screw cap 25 thus allowing the piston rod 14 to be withdrawn.

Should, however, the piston rod 14 be pushed in the direction of the screw cap 25 the wedges 36 will detent between the wedging 35 of the plug 20 and the surfaces 19 of the piston rod 14. This detent supports the action of the springs 37 forcing the wedges 36 from the rear against the wedging 35 tapered forwards. Wedges 36 are also tapered forwards and feature not only locking surfaces adapted to the surface of the piston rod 14 on the inside, but also wedging adapted to the conical surfaces 35 on the outside. Wedges 36 could also be provided all around the piston rod 14 when the latter is roughened all around.

The functioning of the described blood extraction devices is as follows:

When assembled in manufacture the annular plug 20, when in one piece and formed as shown in FIGS. 1 and 3, is first mounted on the rear end of the piston rod 14 in a way as described further below.

The plug 20 is then snapped into place already over the rearmost tooth 41''' before detenting in the rear end of the extraction cylinder 11 as shown in FIG. 1 or it remains on the piston rod piece between the rear end of the ratchet toothing 16 and the handle 24 provided at the end of the piston rod 14.

The piston together with the piston rod 14 and the mounted plug 20 is then inserted into the rear end of the extraction cylinder 11, but only as far so that the plug 20 still protrudes from the rear end of the extraction cylinder 11, i.e. without detenting into place within.

Then the screw cap 25 is screwed into place and vacuum-testing done by withdrawing the piston rod 14, releasing the piston after a certain withdrawal movement and then checking how far it returns forward towards its original position due to the vacuum generated. Should the device be leaking anywhere the piston will not fully attain its original position after being released and the extraction cylinder involved can either be repaired or considered a reject. Once the vacuum-test is successful the plug 20 is pushed sufficiently forward until it snaps into place in the rear end of the extraction cylinder 11. This is best not done until the piston 15 is in the forwardmost position in the extraction cylinder 11. If the ratchet key 17 has already detented behind the rearmost tooth 41''' (FIG. 1) the plug 20 can be moved forward by forwarding the piston rod 14, this necessitating, however, brief venting by slightly backing off the screw caps 25. However, as already mentioned, it is better practice to arrange the plug 20 free to slide between the handle 24 and the toothing 16 because this way the piston 15 can first be brought into the forwardmost position with the screw cap 25 still unscrewed, i.e. then screwing on the screw cap 25 and carrying out the vacuum-test in the manner as already described. The plug 20 is then free to detent in the rear end of the extraction cylinder 11 separately with the piston 15 already in its final position.

The procedure for extracting blood is then as follows:

The guide sleeve 27 is mounted on the boss 26 (FIG. 2) the rear part 12a of the needle 12 piercing the diaphragm 22. The vein can then be punctured and blood extracted by withdrawing the piston 15. In doing so, the ratchet key 17 as shown in FIG. 1 detents from one tooth to the next of the ratchet toothing 16. If the handle 24 is released or should it be attempted to move it in the opposite direction towards the screw cap 25 this is prevented by the ratchet key 17 locking in the tooth 41 present at that time of the ratchet toothing 16. The same applies accordingly to embodiment (FIG. 5) where the wedges 36 prevent a reversal of the movement of the piston rod in the direction of the screw cap 25.

The invention is thus also suitable for creating a vacuum by retracting the piston rod 14 before the guide sleeve 27 is mounted on the boss 26. Whilst in known blood extraction devices of this kind the piston must first be locked into place in the fully retracted position by a companion ratchet of the extraction cylinder 11, the invention provides locking even when the piston 15 is retracted only slightly so that creation of the vacuum can be interrupted in every retracted position of the piston 15, thus making it possible to create even a much weaker vacuum than attainable with the piston 15 fully retracted which can be of advantage e.g. with patients having poor or sensitive veins. In this way the amount of blood extracted in vacuum extraction can also be limited as desired, there being no possibility for the vacuum to collapse due to the one-way coaxial means provided, should the piston be forwarded either intentionally or accidentally.

The invention thus prevents not only intentional or unintentional retraction of the piston 15 but also permits creating and maintaining the desirable vacuum within the extraction cylinder 11 precisely.

To be able to fit the plug 20 particularly easily, to the extent that it surrounds the piston rod 14 as illustrated in the examples of the embodiments, it can be split into two along an axial parting line 21 as shown in FIG. 4 and both parts fitted around the piston rod 14 suitably during assembly.

It is, however, also possible to unscrew the handle 24 (FIGS. 1, 3) or the rear end-piece 14' of the piston rod 14, to then mount the plug 20 from the rear on the untoothed end position of the piston rod 14 before screwing the handle 24 or the end-piece 14' back on.

The piston can also feature an unround cross-section passing through a suitable unround guide opening 13 in the plug 20 to thus ensure perfect angular positioning of the piston rod 14 relative to the plug 20.

When the piston 15 is fully retracted the screwed-in piston rod 14 as shown in FIG. 1 can be screwed out, requiring however, the piston 15 to be locked in place in the rear end of the extraction cylinder 11 in a manner not illustrated. In addition, the portion 40 ahead of the ratchet toothing 16 must have a cross-section to permit turning of the piston rod 14 relative to the fixed piston 15 when the latter is fully retracted.

Figure 6:
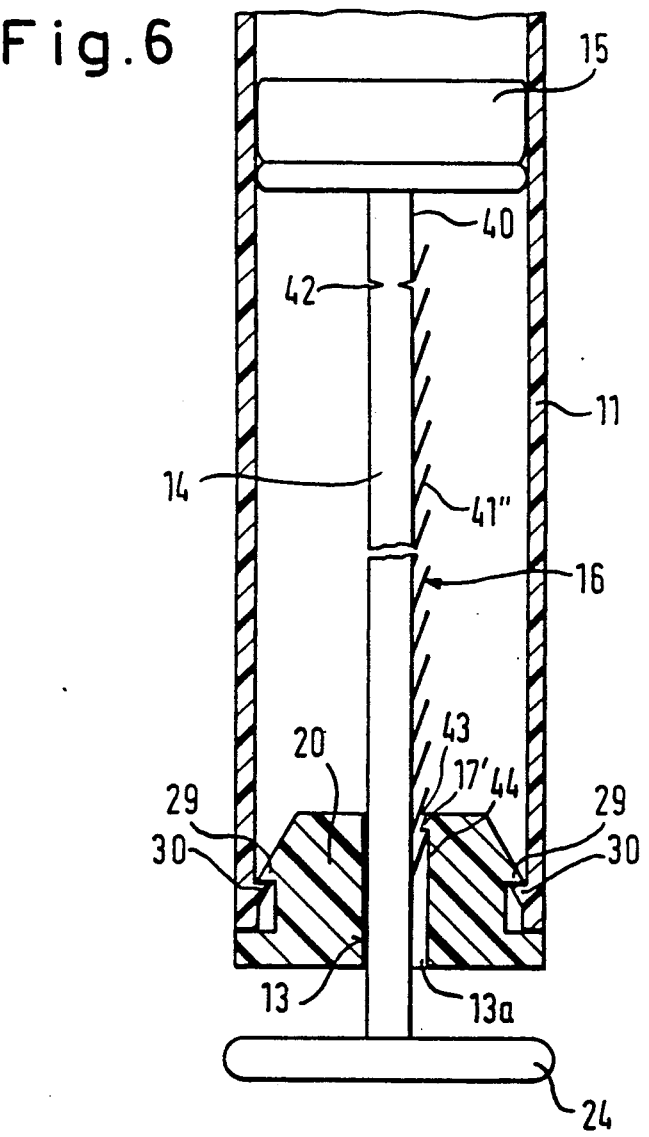

It is, however, also possible that the piston 15 is locked in its most retracted position by the forwardmost tooth 41' of the ratchet toothing 16 detenting behind the ratchet key 17 and then by breaking off the piston rod 14 at an intended position 42 behind the first tooth 41'. Tooth 41' can thus, one and the same, be used to prevent return movement of the piston 15 as well as to lock the piston 15 in the fully retracted position. As indicated by FIG. 6 the toothing 16 provided on the piston rod 14 comprises a row of spring lugs 41'' arranged along the piston rod 14, extending forwards and away from the piston rod 14 in equal spacing. These spring lugs 41'' are formed stiff to compression forces but able to spring-retract radially inwards towards the piston rod 14.

Instead of the ratchet key 17 as shown ins FIGS. 1 and 3 an annular shoulder 17' is provided on the plug 20 in the region of the toothing 16 projecting rigidly into the space 13a radially inwards, this shoulder being spaced 43 from the piston rod 14 so that when the piston rod 14 is retracted the spring lugs 41'' are able to pass through the gap stemming from the space 43 by spring-contraction before snapping into place behind the annular shoulder 17' as shown in FIG. 6 for the rearmost spring lug.

A supporting wall 44 extending rearwards and running parallel to the piston rod 14 is in radial outward connection with the end of the annular shoulder 17'. This supporting wall 44 is in contact with the spring lugs 41'' snapped into place behind the annular shoulder 17' radially and inwards. This arrangement prevents, for instance, radial unspringing of the spring lug in place behind the shoulder 17' when the piston rod 14 is forwarded out of the position as shown in FIG. 6.

When the piston 15 or the piston rod 14 is retracted from the position as shown in FIG. 6 the spring lugs 41'' snap into place, one after the other, behind the rigid annular shoulder 17' and when the movement is reversed the spring lug 41'' which is just behind the annular shoulder 17' mates in the space between the annular shoulder 17' and the supporting wall 44 thus making reversed movement impossible in this example of an embodiment too.

I claim:

1. A blood extraction device having an extraction cylinder, featuring a forward end for attaching a needle and a rear end featuring an axial guide opening for a piston rod; a piston rod; said piston rod (14) having a front end and a handle end; a piston; said piston rod together with said piston arranged for axial sliding in the extraction cylinder, said piston secured detachably to the front end of the piston rod; one-way coacting means provided to act over substantially the full travel of said piston, for permitting movement of said piston substantially in one direction from the forward end of the extraction cylinder to the rear end while substantially preventing movement in the opposite direction; rotational control means for preventing the disengagement of said one-way coacting means.

2. A device according to claim 1, wherein the one-way coacting means (16,17; 18,19) are arranged between the piston rod (14) and the rear end of the extraction cylinder (11).

3. A device according to claim 2, wherein the one-way coacting means comprise at least one ratchet toothing (16) running along and located on the piston rod (14) and at least one ratchet stop (17) acting on said toothing (16) and located at the rear end of the extraction cylinder (11).

4. A device according to claim 3, wherein the teeth (41) of the ratchet toothing (16) are non-elastic and the ratchet stop (17) has spring-loaded contact with the ratchet toothing (16).

5. A device according to claim 3, wherein the teeth (41) of the ratchet toothing (16) are spring lugs (41″) slanting forward away from the piston rod (14) which interact with a fixed ratchet shoulder (17′) constituting the ratchet stop and extending at right angles to the elongation of the piston rod (14).

6. A device according to claim 3 wherein the rotational control means are formed by the ratchet toothing (16) mating in a radial notch (34) having side flanks (33) and arranged unfree to turn with respect to the extraction cylinder (11).

7. A device according to claim 2, wherein the one-way coacting means comprise locking means (18) arranged at one end of the extraction cylinder and acting in one direction and consisting of locking wedges (36) and the surface (19) of the piston rod arranged radially opposite and preferably roughened.

8. A device according to claim 7, wherein the piston rod (14) is roughened on all sides and the locking means (36) are arranged around the piston rod (14).

9. A device according to one of the claims 2, wherein the piston rod (14) has an unround cross-section passing through a suitable unround guide opening (13) at the rear end of the extraction cylinder (11).

10. A device according to claim 8 wherein the one-way coacting means (17, 18) at the rear of the extraction cylinder (11) are provided in a plug (20) for insertion in or on the rear end of the extraction cylinder (11) and featuring the guide opening (13) for the piston rod (14) and which can be fixed in the end of the extraction cylinder (11) so that it remains in position when removing or inserting the piston rod from and into the extraction cylinder (11), respectively.

11. A device according to claim 10, wherein the plug (20) locks into place from the rear when inserted in the rear end of the extraction cylinder.

12. A device according to claim 10, wherein the plug (20) surrounds the piston rod (14).

13. A device according to claim 12, wherein the plug (20) is split axially into two parts, permitting insertion to enclose the piston rod (14).

14. A device according to claim 10, wherein the handle (14) or end-piece (14′) of the piston rod (14) can be removed so that the plug (20) can be inserted on the piston rod (14) at its rear end.

15. A blood extraction device having a piston rod; an extraction cylinder, featuring a forward end for attaching a needle and a rear end featuring an axial guide opening for said piston rod; said, piston rod having a front end and a handle end; a piston said piston rod together with said piston arranged for axial sliding in the extraction cylinder said piston secured detachably to the front end of the piston rod; a rotationally symmetrical one-way coacting means provided to act over substantially the full travel of said piston for permitting movement of said piston substantially in one direction from the forward end of the extraction cylinder to the rear while substantially preventing movement in the opposite direction.

16. The blood extraction device of claim 15 wherein the one-way coacting means at the rear of the extraction cylinder are provided integral with a plug adapted for insertion in the rear end of the extraction cylinder; the plug providing the guide opening for the piston rod; and the plug fixedly attachable in the end of the extraction cylinder.

* * * * *